United States Patent
Boday

(10) Patent No.: US 8,685,333 B2
(45) Date of Patent: Apr. 1, 2014

(54) PORTABLE DEVICE FOR POSITIVELY PRESSURIZING A STRUCTURE WITH HIGH LEVELS OF OZONE GAS THAT IS INTERNALLY GENERATED, TO ERADICATE A PLURALITY OF PESTS, VIRUSES, MOLDS, MOLD SPORES, FUNGI, BACTERIA AND ODORS

(76) Inventor: Charles Boday, Oberlin, OH (US)

(*) Notice: Subject to any disclaimer, the term of this patent is extended or adjusted under 35 U.S.C. 154(b) by 174 days.

(21) Appl. No.: 13/302,995

(22) Filed: Nov. 22, 2011

(65) Prior Publication Data

US 2012/0128543 A1  May 24, 2012

Related U.S. Application Data

(60) Provisional application No. 61/416,704, filed on Nov. 23, 2010.

(51) Int. Cl.
*B01J 19/08* (2006.01)

(52) U.S. Cl.
USPC ........................................ 422/186.3

(58) Field of Classification Search
USPC ........................................ 422/186.3
See application file for complete search history.

(56) References Cited

U.S. PATENT DOCUMENTS

| | | | | |
|---|---|---|---|---|
| 5,824,274 | A * | 10/1998 | Long | 708/140 |
| 5,837,207 | A * | 11/1998 | Summers | 422/121 |
| 7,740,686 | B2 * | 6/2010 | Metteer | 95/58 |
| 8,277,740 | B2 * | 10/2012 | Pattee | 422/186.07 |

* cited by examiner

*Primary Examiner* — Kishor Mayekar
(74) *Attorney, Agent, or Firm* — Michael Ries

(57) ABSTRACT

A portable ozone gas generating device that includes one or more transformers is disclosed. The portable ozone gas generating device generates a plurality of high levels of ozone gas to eradicate a plurality of pests, odors and undesired microorganisms, one or more generator cells that are utilized by the device to eradicate the plurality of pests and undesired microorganisms and an ozone hose or other conduit that directs air that is forced across the generator cell. The device also includes a blower that is a powerful high volume high pressure blower, turbine or fan that provides power to the directed ozone air required to positively pressurize a structure to eradicate the plurality of pests, odors and undesired microorganisms, a large diameter flexible undegradable ozone rated hose and a filtration system and an adjustable disposable aperture airlock that connects the structure with the device.

16 Claims, 1 Drawing Sheet

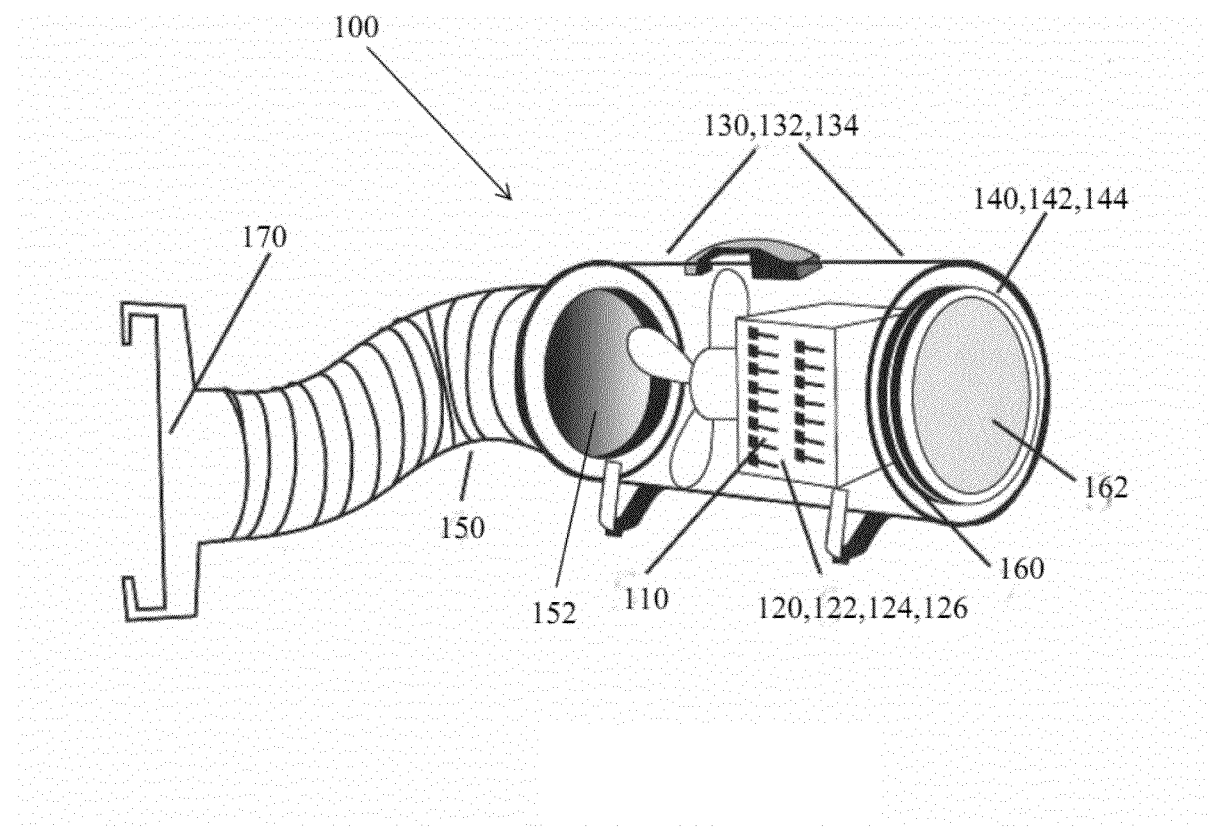

_US 8,685,333 B2_

PORTABLE DEVICE FOR POSITIVELY PRESSURIZING A STRUCTURE WITH HIGH LEVELS OF OZONE GAS THAT IS INTERNALLY GENERATED, TO ERADICATE A PLURALITY OF PESTS, VIRUSES, MOLDS, MOLD SPORES, FUNGI, BACTERIA AND ODORS

This application claims priority to U.S. Provisional Application 61/416,704 filed on Nov. 23, 2010, the entire disclosure of which is incorporated by reference.

TECHNICAL FIELD & BACKGROUND

There is a plurality of known uses for ozone generation devices at high volumes. One problem with the existing devices is that they only generate ozone in high volumes for the elimination of pests and microorganisms, but do not penetrate into relatively tinier recessed areas of the structure being cleaned.

It is an object of the present invention to provide a portable ozone gas generating device that positively pressurizes a structure with a plurality of relatively high levels of ozone gas to eradicate a plurality of pests and undesired microorganisms.

It is an object of the present invention to provide a portable ozone gas generating device that positively pressurizes a structure with a plurality of relatively high levels of ozone gas to eradicate a plurality of pests and undesired microorganisms without leaving behind one or more harmful residues.

It is an object of the present invention to provide a portable ozone gas generating device that positively pressurizes a structure with a plurality of relatively high levels of ozone gas that will penetrate into relatively tiny hidden spaces where unpressurized liquid and gas based eradicate dispersants cannot penetrate.

What is really needed is a portable ozone gas generating device that positively pressurizes a structure with a plurality of relatively high levels of ozone gas to eradicate a plurality of pests and undesired microorganisms without leaving behind one or more harmful residues that positively pressurizes a structure with a plurality of relatively high levels of ozone gas that will penetrate into relatively tiny hidden spaces where unpressurized liquid and gas based eradicate dispersants cannot penetrate.

BRIEF DESCRIPTION OF THE DRAWINGS

The present invention will be described by way of exemplary embodiments, but not limitations, illustrated in the accompanying drawings in which like references denote similar elements, and in which:

FIG. 1 illustrates a side perspective view of a portable ozone gas generating device, in accordance with one embodiment of the present invention.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention, however, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

FIG. 1 illustrates a side perspective view of a portable ozone gas generating device 100, in accordance with one embodiment of the present invention.

The portable ozone gas generating device 100 positively pressurizes a structure with a plurality of relatively high levels of ozone gas to eradicate a plurality of pests and undesired microorganisms without leaving behind one or more harmful residues that will penetrate into relatively tiny hidden spaces where unpressurized liquid and gas based eradicate dispersants cannot penetrate.

The portable ozone gas generating device 100 includes one or more transformers 110, one or more generator cells 120, an ozone hose or other conduit 130, a blower 140, a flexible hose 150, a filtration system 160 and an adjustable aperture airlock 170.

The one or more transformers 110 can be a single transformer or a series of transformers. The one or more transformers 110 provide and can increase voltage levels that are needed to generate the relatively high levels of ozone gas to eradicate the plurality of pests and undesired microorganisms intended to be eradicated. The undesired microorganisms include viruses, molds, mold spores, fungi, bacteria and other suitable undesired microorganisms. The one or more generator cells 120 can be a single generator cell or a series of generator cells. The one or more generator cells 120 typically utilized by the portable ozone gas generating device 100 includes a dielectric and electrified material 122 or a lamp bulb 124 which when powered by high voltage electricity or using ultraviolet or UV lamp bulb 126 generates ozone at the relatively high levels necessary to eradicate the plurality of pests and undesired microorganisms intended to be eradicated. The ozone hose or other conduit 130 can be a generation chamber 132 that directs air that is forced across the generator cell 120 and is in an enclosed housing 134 to protect the ozone hose or other conduit 130 or the generation chamber 132. The blower 140 can be a turbine 142 or a fan 144 and is a relatively powerful high volume high pressure blower 140, turbine 142 or fan 144 and provides power to the directed ozone air required to positively pressurize a structure to eradicate the plurality of pests and undesired microorganisms intended to be eradicated. The flexible hose 150 is a suitably ozone rated hose 150 that is also a relatively large diameter hose. The flexible hose 150 provides a conduit from the outlet aperture 152 of the portable ozone gas generating device 100 to the adjustable aperture airlock 170 and is undegradable by the ozone gas. The filtration system 160 includes a pre-filter 162 and keeps the generator cells 120 free of dust and debris and prevents accumulation of dust on the generator cell 120 or the lamp bulb 124 or the UV lamp bulb 126, thereby extending the longevity of the portable ozone gas generating device 100. The adjustable aperture airlock 170 is typically disposable and connects the structure or other suitable building or area with the flexible hose 150 to the portable ozone gas generating device 100.

The portable ozone gas generating device is a portable device that generates a relatively high milligram per hour ozone gas output and directs it into a structure at a relative high volume and sufficient pressure to induce positive pressurization of ozone gas in a structure or dedicated area in a structure, sufficient to create a level of ozone to kill or eliminate a plurality of harmful pests and microorganisms such as viruses, molds, mold spores, fungi and bacteria. By creating positive pressure, the ozone gas is expelled into a plurality of relatively tiny cracks, crevices and cul-de-sacs that exist in every structure. It eliminates the ability for these microorganisms or pests to hide in areas that are inaccessible to a liquid. The application of the portable ozone gas generating device is relatively very broad that can be applied and utilized in a plurality of environments.

The portable ozone gas generating device generates relatively high levels of ozone gas using one or more existing ozone generating methods and combines these methods for generating relatively high levels of ozone gas with one or more existing methods to move air and create pressure at high volumes. A variety of options exists for individual ozone generation and individual air moving, however both individual ozone generation and individual air moving can be combined into a new machine with one or more new capacities. An integral part of the new ozone generation and individual air moving device is an adjustable aperture airlock which allows the portable ozone gas generating device to couple with a window or a doorway in a structure in order to create an airlock for pressurization of the structure. The ability to pressurize a structure with ozone gas, especially a large structure like or residence or commercial building has a multitude of readably available uses.

All of the components of the portable ozone gas generating device exist in a plurality of environments, settings and variations. However none of the existing traditionally available previously mentioned devices incorporates these components into a single device to accomplish a positive pressurization of a structure or desired area. The combining of the ozone generator cell inside the ozone hose or other conduit and using a high pressure high volume blower, turbine or fan and the flexible ozone rated hose is utilized as well to connect to a wide variety of shapes with an adjustable disposable aperture. Also the power and CFM capacity is significantly different when being combined with an ozone generator cell inside a tunnel. Additionally the hose and adjustable aperture airlock allows for ozone to be expelled into relatively tiny spaces in a structure where the use of typical ozone generators allows only the creation of ozone in an ambient air environment inside of a structure. By creating positive pressurization, the ozone gas is forced through and out of the structure in any area that is not air tight. The ozone encounters all of the surfaces that exist on the inside of the structure and as well as into relatively tiny areas where liquid or smoke based dispersants cannot penetrate.

In operating the portable ozone gas generating device, the transformer electrifies the generator cells inside the ozone hose or other conduit, the ozone hose or other conduit directs the moving air that is created by the blower fan or turbine and forces it through the ozone hose or other conduit and out of the portable ozone gas generating device into the large diameter flexible ozone rated hose through the adjustable aperture air lock and through and into the structure and then out again through the unsealed places that are not air tight.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A portable ozone gas generating device, comprising:
   one or more transformers that provide and increase one or more voltage levels that are needed to generate a plurality of high levels of ozone gas to eradicate a plurality of pests, odors and undesired microorganisms intended to be eradicated;
   one or more generator cells that are utilized by said portable ozone gas generating device, said one or more generator cells include a lamp bulb which when powered by high voltage electricity generates ozone at a high level necessary to eradicate said plurality of pests, odors and undesired microorganisms intended to be eradicated;
   an ozone hose or other conduit that directs ozone air that is forced across said generator cell;
   a blower that is a powerful high volume high pressure blower that provides power to said directed ozone air required to positively pressurize a structure to eradicate said plurality of pests, odors and undesired microorganisms intended to be eradicated, wherein said blower is a powerful high volume high pressure turbine;
   a large diameter flexible ozone rated hose that provides a conduit from an outlet of said portable ozone gas generating device, wherein said large diameter flexible ozone rated hose is undegradable by said ozone gas;
   a filtration system with a pre-filter that keeps said one or more generator cells and said lamp bulb free of dust, dust accumulation and debris, extending longevity of said portable ozone gas generating device; and
   an adjustable aperture airlock connected to said portable ozone gas generating device with said flexible hose, wherein said adjustable aperture airlock is disposable, said adjustable aperture airlock allows said portable ozone gas generating device to couple with a window or a doorway in a structure in order to create an airlock for pressurization of the structure.

2. The device according to claim 1, wherein said one or more transformers are a single transformer or a series of transformers.

3. The device according to claim 1, wherein said undesired microorganisms are selected from the group consisting of any combination of one or more viruses, one or more molds, one or more mold spores, one or more fungi or one or more bacteria.

4. The device according to claim 1, wherein said one or more generator cells are a single generator cell or a series of generator cells.

5. The device according to claim 1, wherein said one or more generator cells is an ultraviolet lamp bulb.

6. The device according to claim 1, wherein said ozone hose or other conduit is in an enclosed housing to protect said ozone hose or other conduit.

7. The device according to claim 1, wherein said blower is a powerful high volume high pressure fan.

8. The device according to claim 1, wherein said large diameter flexible ozone rated hose provides said conduit from an outlet of said portable ozone gas generating device to said adjustable aperture airlock.

9. The device according to claim 1, wherein said lamp bulb is an ultraviolet lamp bulb.

10. A portable ozone gas generating device, comprising:
one or more transformers that provide and increase one or more voltage levels that are needed to generate a plurality of high levels of ozone gas to eradicate a plurality of pests and undesired microorganisms intended to be eradicated;
one or more generator cells that are utilized by said portable ozone gas generating device that include a lamp bulb which when powered by high voltage electricity generates ozone at a high level necessary to eradicate said plurality of pests and undesired microorganisms intended to be eradicated;
an ozone hose or other conduit that directs air that is forced across said generator cell;
a blower that is a powerful high volume high pressure blower, a powerful high volume high pressure turbine or a powerful high volume high pressure fan that provides power to said directed ozone air required to positively pressurize a structure to eradicate said plurality of pests and undesired microorganisms intended to be eradicated;
a large diameter flexible undegradable ozone rated hose that provides a conduit from said transformer of said portable ozone gas generating device;
a filtration system with a pre-filter that keeps said one or more generator cells and said lamp bulb free of dust, dust accumulation and debris, extending longevity of said portable ozone gas generating device; and
an adjustable disposable aperture airlock that connects said structure with said flexible hose to said portable ozone gas generating device, said adjustable aperture airlock allows said portable ozone gas generating device to couple with a window or a doorway in a structure in order to create an airlock for pressurization of the structure.

11. The device according to claim 10, wherein said one or more transformers are a single transformer or a series of transformers.

12. The device according to claim 10, wherein said undesired microorganisms are selected from the group consisting of any combination of one or more viruses, one or more molds, one or more mold spores, one or more fungi or one or more bacteria.

13. The device according to claim 10, wherein said one or more generator cells are a single generator cell or a series of generator cells.

14. The device according to claim 10, wherein said one or more generator cells include an ultraviolet lamp bulb.

15. The device according to claim 10, wherein said ozone hose or other conduit is in an enclosed housing to protect said ozone hose or other conduit.

16. The device according to claim 10, wherein said large diameter flexible ozone rated hose provides said conduit from said transformer to said adjustable aperture airlock.

* * * * *